US008145500B2

(12) United States Patent
Matisonn et al.

(10) Patent No.: US 8,145,500 B2
(45) Date of Patent: Mar. 27, 2012

(54) DATA PROCESSING SYSTEM FOR ACCURATELY CALCULATING A POLICYHOLDER'S DISCOUNT IN A MEDICAL INSURANCE PLAN AND A METHOD THEREFOR

(75) Inventors: Shaun Matisonn, Gauteng (ZA); Samuel Shlomo Greenblatt, Gauteng (ZA); Timothy Berghorst, Gauteng (ZA)

(73) Assignee: Discovery Holdings Limited, Sandton (ZA)

( * ) Notice: Subject to any disclaimer, the term of this patent is extended or adjusted under 35 U.S.C. 154(b) by 1267 days.

(21) Appl. No.: 11/189,647

(22) Filed: Jul. 26, 2005

(65) Prior Publication Data

US 2006/0041454 A1    Feb. 23, 2006

(30) Foreign Application Priority Data

Jul. 26, 2004 (ZA) .................................. 2004/5935

(51) Int. Cl.
*G06Q 10/00* (2006.01)
*G06Q 50/00* (2006.01)
(52) U.S. Cl. .............................................. 705/2; 705/4
(58) Field of Classification Search ...................... 705/2
See application file for complete search history.

(56) References Cited

U.S. PATENT DOCUMENTS

| | | |
|---|---|---|
| 4,556,216 A | 12/1985 | Pitkanen |
| 4,699,375 A | 10/1987 | Appelbaum et al. |
| 4,831,526 A | 5/1989 | Luchs et al. |
| 4,837,693 A | 6/1989 | Schotz |
| 4,860,275 A | 8/1989 | Kakinuma et al. |
| 4,975,840 A | 12/1990 | DeTore et al. |
| 5,062,645 A | 11/1991 | Goodman et al. |
| 5,136,502 A | 8/1992 | Van Remortel et al. |
| 5,297,026 A | 3/1994 | Hoffman |

(Continued)

FOREIGN PATENT DOCUMENTS

AU    2001/276596    3/2003

(Continued)

OTHER PUBLICATIONS

U.S. Appl. No. 09/876,311, filed Jun. 7, 2001.

(Continued)

*Primary Examiner* — Gerald J. O'Connor
*Assistant Examiner* — Hiep V Nguyen
(74) *Attorney, Agent, or Firm* — Fleit Gibbons Gutman Bongini & Bianco, PL; Paul D. Bianco; Martin Fleit (57) ABSTRACT

A data processing system for accurately calculating a discount in a medical insurance plan comprises a premiums module adapted to access data regarding the amount of premiums paid by a policyholder of the medical insurance plan for a predetermined period. A claims module is adapted to access data regarding the amount of claims paid by the medical insurance plan to the policyholder for the predetermined period, the claims module being further adapted to access data to determine if there have been any claims submitted by a policyholder which have not yet been paid, and if so to apply a set of rules to each submitted claim which has not been paid to determine if it is likely to be paid, and if the claim is likely to be paid then adding the amount of the claim to the amount of claims already paid for the predetermined period. Finally, a discount module adapted to receive data from the premiums module and the claims module and to use the data to calculate a discount amount.

20 Claims, 6 Drawing Sheets

U.S. PATENT DOCUMENTS

| | | |
|---|---|---|
| 5,301,105 A | 4/1994 | Cummings, Jr. |
| 5,324,077 A | 6/1994 | Kessler et al. |
| 5,429,506 A | 7/1995 | Brophy et al. |
| 5,490,260 A | 2/1996 | Miller et al. |
| 5,542,420 A | 8/1996 | Goldman et al. |
| 5,549,117 A | 8/1996 | Tacklind et al. |
| 5,550,734 A | 8/1996 | Tarter et al. |
| 5,574,803 A | 11/1996 | Gaborski et al. |
| 5,631,828 A | 5/1997 | Hagan |
| 5,655,085 A | 8/1997 | Ryan et al. |
| 5,655,997 A | 8/1997 | Greenberg et al. |
| 5,692,501 A | 12/1997 | Minturn |
| 5,722,418 A | 3/1998 | Bro |
| 5,745,893 A | 4/1998 | Hill et al. |
| 5,752,236 A | 5/1998 | Sexton et al. |
| 5,774,883 A | 6/1998 | Andersen et al. |
| 5,832,467 A | 11/1998 | Wavish |
| 5,867,821 A | 2/1999 | Ballantyne et al. |
| 5,890,129 A | 3/1999 | Spurgeon |
| 5,933,809 A | 8/1999 | Hunt et al. |
| 5,933,815 A | 8/1999 | Golden |
| 5,937,387 A * | 8/1999 | Summerell et al. ............ 705/2 |
| 5,987,434 A | 11/1999 | Libman |
| 5,991,744 A | 11/1999 | Dicresce |
| 6,039,688 A | 3/2000 | Douglas et al. |
| 6,049,772 A | 4/2000 | Payne et al. |
| 6,085,174 A | 7/2000 | Edelman |
| 6,085,976 A | 7/2000 | Sehr |
| 6,108,641 A | 8/2000 | Kenna et al. |
| 6,112,986 A | 9/2000 | Berger et al. |
| 6,151,586 A | 11/2000 | Brown |
| 6,169,770 B1 | 1/2001 | Henely |
| 6,230,142 B1 | 5/2001 | Benigno et al. |
| 6,338,042 B1 | 1/2002 | Paizis |
| 6,385,589 B1 | 5/2002 | Trusheim et al. |
| 6,513,532 B2 | 2/2003 | Mault |
| 6,587,829 B1 | 7/2003 | Camarda |
| 6,602,469 B1 | 8/2003 | Maus et al. |
| 6,611,815 B1 | 8/2003 | Lewis et al. |
| 6,965,868 B1 | 11/2005 | Bednarek |
| 7,319,970 B1 | 1/2008 | Simone |
| 7,380,707 B1 | 6/2008 | Fredman |
| 7,383,223 B1 | 6/2008 | Dilip et al. |
| 7,624,032 B2 | 11/2009 | Rabson et al. |
| 7,630,937 B1 | 12/2009 | Mo et al. |
| 7,685,007 B1 | 3/2010 | Jacobson |
| 7,797,175 B2 | 9/2010 | Luedtke |
| 2001/0037214 A1 | 11/2001 | Raskin et al. |
| 2001/0053984 A1 | 12/2001 | Joyce |
| 2002/0002495 A1 | 1/2002 | Ullman |
| 2002/0013717 A1* | 1/2002 | Ando et al. ............ 705/4 |
| 2002/0016923 A1 | 2/2002 | Knaus |
| 2002/0029158 A1 | 3/2002 | Wolff et al. |
| 2002/0035486 A1 | 3/2002 | Huyn et al. |
| 2002/0038310 A1 | 3/2002 | Reitberg |
| 2002/0042763 A1 | 4/2002 | Pillay |
| 2002/0049617 A1 | 4/2002 | Lencki et al. |
| 2002/0055859 A1 | 5/2002 | Goodman et al. |
| 2002/0087364 A1 | 7/2002 | Lerner et al. |
| 2002/0103678 A1 | 8/2002 | Burkhalter et al. |
| 2002/0111827 A1 | 8/2002 | Levin et al. |
| 2002/0116231 A1 | 8/2002 | Hele et al. |
| 2002/0116266 A1 | 8/2002 | Marshall |
| 2002/0138309 A1 | 9/2002 | Thomas |
| 2002/0152097 A1 | 10/2002 | Javors |
| 2002/0184129 A1 | 12/2002 | Arena |
| 2003/0009355 A1 | 1/2003 | Gupta |
| 2003/0028483 A1 | 2/2003 | Sanders et al. |
| 2003/0055767 A1 | 3/2003 | Tamura |
| 2003/0065561 A1 | 4/2003 | Brown |
| 2003/0078815 A1 | 4/2003 | Parsons |
| 2003/0120561 A1 | 6/2003 | Sherman |
| 2003/0120570 A1 | 6/2003 | Dellinger |
| 2003/0135391 A1 | 7/2003 | Edmundson |
| 2003/0149596 A1 | 8/2003 | Bost |
| 2003/0194071 A1 | 10/2003 | Ramian |
| 2003/0200101 A1 | 10/2003 | Adler |
| 2003/0200142 A1 | 10/2003 | Hicks et al. |
| 2003/0208385 A1 | 11/2003 | Zander |
| 2003/0212579 A1 | 11/2003 | Brown |
| 2003/0233278 A1* | 12/2003 | Marshall ............ 705/14 |
| 2004/0030625 A1 | 2/2004 | Radson et al. |
| 2004/0039608 A1 | 2/2004 | Mazur |
| 2004/0039611 A1 | 2/2004 | Hong et al. |
| 2004/0059608 A1 | 3/2004 | Gore et al. |
| 2004/0088219 A1* | 5/2004 | Sanders et al. ............ 705/14 |
| 2004/0138928 A1 | 7/2004 | Monk |
| 2004/0267570 A1 | 12/2004 | Becker et al. |
| 2005/0010453 A1 | 1/2005 | Terlizzi |
| 2005/0033609 A1 | 2/2005 | Yang |
| 2005/0038679 A1 | 2/2005 | Short |
| 2005/0060209 A1 | 3/2005 | Hill |
| 2005/0071205 A1 | 3/2005 | Terlizzi |
| 2005/0102172 A1* | 5/2005 | Sirmans, Jr. ............ 705/4 |
| 2005/0131742 A1 | 6/2005 | Hoffman et al. |
| 2005/0222867 A1 | 10/2005 | Underwood |
| 2005/0222877 A1 | 10/2005 | Radson et al. |
| 2005/0222878 A1 | 10/2005 | Radson et al. |
| 2005/0228692 A1* | 10/2005 | Hodgdon ............ 705/2 |
| 2005/0234742 A1 | 10/2005 | Hodgdon |
| 2005/0240449 A1 | 10/2005 | Rabson et al. |
| 2005/0256748 A1 | 11/2005 | Gore et al. |
| 2005/0288971 A1 | 12/2005 | Cassandra |
| 2006/0041454 A1 | 2/2006 | Matisonn et al. |
| 2006/0064320 A1 | 3/2006 | Postrel |
| 2006/0074801 A1 | 4/2006 | Pollard et al. |
| 2006/0111944 A1 | 5/2006 | Sirmans |
| 2006/0129436 A1 | 6/2006 | Short |
| 2006/0143055 A1 | 6/2006 | Loy |
| 2006/0218011 A1 | 9/2006 | Walker et al. |
| 2006/0218023 A1 | 9/2006 | Conrad |
| 2007/0027726 A1 | 2/2007 | Warren et al. |
| 2007/0050215 A1 | 3/2007 | Kil |
| 2007/0050217 A1 | 3/2007 | Holden, Jr. |
| 2007/0061237 A1 | 3/2007 | Merton |
| 2007/0094125 A1 | 4/2007 | Izyayev |
| 2007/0112669 A1 | 5/2007 | Snyder |
| 2007/0136093 A1 | 6/2007 | Rankin |
| 2007/0233512 A1 | 10/2007 | Gore |
| 2008/0046382 A1 | 2/2008 | Metz |
| 2008/0071600 A1 | 3/2008 | Johnson |
| 2008/0082372 A1 | 4/2008 | Burch |
| 2008/0154650 A1 | 6/2008 | Matisonn et al. |
| 2008/0172214 A1 | 7/2008 | Col |
| 2008/0189141 A1 | 8/2008 | Gore et al. |
| 2008/0197185 A1 | 8/2008 | Cronin et al. |
| 2008/0243558 A1 | 10/2008 | Gupte |
| 2008/0255979 A1 | 10/2008 | Slutzky et al. |
| 2008/0262877 A1 | 10/2008 | Hargroder |
| 2008/0312969 A1 | 12/2008 | Raines |
| 2009/0024419 A1 | 1/2009 | McClellan et al. |
| 2009/0024478 A1 | 1/2009 | Dixon |
| 2009/0076903 A1 | 3/2009 | Schwarzberg et al. |
| 2009/0105550 A1 | 4/2009 | Rothman |
| 2009/0150189 A1 | 6/2009 | Barron |
| 2009/0150192 A1 | 6/2009 | Gore et al. |
| 2009/0198525 A1 | 8/2009 | Gore et al. |
| 2009/0204441 A1 | 8/2009 | Read |
| 2009/0204446 A1 | 8/2009 | Simon |
| 2009/0240532 A1 | 9/2009 | Gore et al. |
| 2009/0259497 A1 | 10/2009 | Gore et al. |
| 2009/0265183 A1 | 10/2009 | Pollard et al. |
| 2009/0299773 A1 | 12/2009 | Gore et al. |
| 2009/0299774 A1 | 12/2009 | Gore et al. |
| 2009/0299775 A1 | 12/2009 | Gore et al. |
| 2009/0299776 A1 | 12/2009 | Gore et al. |
| 2009/0307015 A1 | 12/2009 | Gore et al. |
| 2010/0023354 A1 | 1/2010 | Gore et al. |
| 2010/0023384 A1 | 1/2010 | Pollard et al. |
| 2010/0049541 A1 | 2/2010 | Pollard et al. |

FOREIGN PATENT DOCUMENTS

| | | |
|---|---|---|
| AU | 2005/323847 | 2/2007 |
| AU | 2007/257457 | 1/2009 |
| AU | 2007/257458 | 1/2009 |
| AU | 2007/257546 | 1/2009 |
| AU | 2007/298514 | 2/2009 |

| | | |
|---|---|---|
| AU | 2007/301521 | 5/2009 |
| CN | 2005/880047059 | 7/2007 |
| EP | 1050821 | 11/2000 |
| IL | 195735 | 12/2008 |
| IL | 195737 | 12/2008 |
| IL | 195738 | 12/2008 |
| WO | 02/47074 | 6/2002 |
| WO | 03/007230 | 1/2003 |
| WO | 2007/141695 | 12/2007 |
| WO | 2007/141696 | 12/2007 |
| WO | 2007/141968 | 12/2007 |
| WO | 2008/035280 | 3/2008 |
| ZA | 98/02005 | 3/1998 |
| ZA | 98/11943 | 12/1998 |
| ZA | 2000/04682 | 9/2000 |
| ZA | 2004/02587 | 4/2004 |
| ZA | 2004/02891 | 4/2004 |
| ZA | 2004/05935 | 7/2004 |
| ZA | 2004/06294 | 8/2004 |
| ZA | 2006/01934 | 3/2006 |
| ZA | 2006/04673 | 6/2006 |
| ZA | 2006/04674 | 6/2006 |
| ZA | 2006/04687 | 6/2006 |
| ZA | 2006/04688 | 6/2006 |
| ZA | 2006/07789 | 9/2006 |
| ZA | 2006/07992 | 9/2006 |
| ZA | 2008-03529 | 4/2008 |
| ZA | 2008/04807 | 6/2008 |
| ZA | 2008/04808 | 6/2008 |
| ZA | 2008/04809 | 6/2008 |
| ZA | 2008/04810 | 6/2008 |
| ZA | 2008/04811 | 6/2008 |
| ZA | 2009/01740 | 3/2009 |

OTHER PUBLICATIONS

U.S. Appl. No. 09/876,311, Final Rejection Oct. 23, 2006.
U.S. Appl. No. 09/876,311, Final Rejection Dec. 16, 2009.
U.S. Appl. No. 09/876,311, Non-Final Rejection Jan. 17, 2006.
U.S. Appl. No. 09/876,311, Non-Final Rejection Nov. 30, 2007.
U.S. Appl. No. 09/876,311, Non-Final Rejection Jul. 9, 2010.
U.S. Appl. No. 09/876,311, Requirement for Restriction May 18, 2007.
U.S. Appl. No. 09/876,311, Requirement for Restriction Jan. 2, 2009.
U.S. Appl. No. 09/876,311, Requirement for Restriction Jan. 16, 2009.
U.S. Appl. No. 09/876,311, Requirement for Restriction Aug. 10, 2009.
U.S. Appl. No. 09/876,311, Response to Office Action Jul. 19, 2006.
U.S. Appl. No. 09/876,311, Response to Office Action Feb. 23, 2007.
U.S. Appl. No. 09/876,311, Response to Office Action Jul. 17, 2007.
U.S. Appl. No. 09/876,311, Response to Office Action May 29, 2008.
U.S. Appl. No. 09/876,311, Response to Office Action Oct. 15, 2008.
U.S. Appl. No. 09/876,311, Response to Office Action Feb. 5, 2009.
U.S. Appl. No. 09/876,311, Response to Office Action May 28, 2009.
U.S. Appl. No. 09/876,311, Response to Office Action Sep. 10, 2009.
U.S. Appl. No. 09/876,311, Response to Office Action May 17, 2010.
U.S. Appl. No. 09/982,274, filed Oct. 17, 2001.
U.S. Appl. No. 09/982,274, Final Rejection Nov. 27, 2006.
U.S. Appl. No. 09/982,274, Final Rejection May 6, 2008.
U.S. Appl. No. 09/982,274, Final Rejection Jun. 9, 2009.
U.S. Appl. No. 09/982,274, Non-Final Rejection Mar. 3, 2006.
U.S. Appl. No. 09/982,274, Non-Final Rejection Aug. 9, 2007.
U.S. Appl. No. 09/982,274, Non-Final Rejection Oct. 17, 2008.
U.S. Appl. No. 09/982,274, Response to Office Action Sep. 6, 2006.
U.S. Appl. No. 09/982,274, Response to Office Action May 29, 2007.
U.S. Appl. No. 09/982,274, Response to Office Actino Jan. 22, 2008.
U.S. Appl. No. 09/982,274, Response to Office Action Aug. 6, 2008.
U.S. Appl. No. 09/982,274, Repsonse to Office Action Feb. 17, 2009.
U.S. Appl. No. 09/982,274, Notice of Appeal filed Sep. 9, 2009.
U.S. Appl. No. 09/982,274, Appeal Brief Filed Nov. 9, 2009.
U.S. Appl. No. 09/982,274, Reply Brief filed Apr. 2, 2010.
U.S. Appl. No. 12/112,165, filed Apr. 30, 2001.
U.S. Appl. No. 10/251,120, filed Sep. 20, 2002.
U.S. Appl. No. 10/251,120, Final Rejection Dec. 31, 2007.
U.S. Appl. No. 10/251,120, Final Rejection Jun. 25, 2009.
U.S. Appl. No. 10/251,120, Non-Final Rejection Mar. 29, 2007.
U.S. Appl. No. 10/251,120, Non-Final Rejection Jan. 5, 2009.
U.S. Appl. No. 10/251,120, Examiner Summary Oct. 21, 2009.
U.S. Appl. No. 10/251,120, Examiner Summary Jul. 6, 2010.
U.S. Appl. No. 10/251,120, Response to Office Action Sep. 28, 2007.
U.S. Appl. No. 10/251,120, Response to Office Action Oct. 7, 2008.
U.S. Appl. No. 10/251,120, Response to Office Action Apr. 6, 2009.
U.S. Appl. No. 10/251,120, Appeal Brief Filed Mar. 24, 2010.
U.S. Appl. No. 12/122,549, filed May 16, 2008.
U.S. Appl. No. 11/198,206, filed Aug. 5, 2005.
U.S. Appl. No. 11/198,206, Final Rejection Jan. 23, 2009.
U.S. Appl. No. 11/198,206, Non-Final Rejection Jun. 30, 2008.
U.S. Appl. No. 11/198,206, Response to Office Action Oct. 30, 2008.
U.S. Appl. No. 12/333,465, filed Dec. 12, 2008.
U.S. Appl. No. 12/262,266, filed Oct. 31, 2008.
U.S. Appl. No. 12/303,388, filed Dec. 4, 2008.
U.S. Appl. No. 12/303,391, filed Dec. 4, 2008.
U.S. Appl. No. 12/303,395, filed Dec. 4, 2008.
U.S. Appl. No. 12/303,399, filed Dec. 4, 2008.
U.S. Appl. No. 12/441,447, filed Mar. 16, 2009.
U.S. Appl. No. 10/344,176, filed Aug. 15, 2003.
U.S. Appl. No. 10/344,176, Final Rejection Oct. 30, 2008.
U.S. Appl. No. 10/344,176, Final Rejection Mar. 2, 2010.
U.S. Appl. No. 10/344,176, Non-Final Rejection Dec. 19, 2007.
U.S. Appl. No. 10/344,176, Non-Final Rejection Jun. 8, 2009.
U.S. Appl. No. 10/344,176, Response to Office Action May 19, 2008.
U.S. Appl. No. 10/344,176, Response to Office Action Mar. 2, 2009.
Rintelman, Mary Jane, "Choice and cost-savings", Credit Union Management, vol. 19, No. 7, pp. 48, 50. Jul. 1996.
Woodard, Kathy, "stay healthy for real fun—and profit", Business First Columbus, vol. 12, No. 19, S.1, p. 13. Jan. 1996.
Spencer, Peter L., "New plan cuts health car costs in half (advantage of health care plan with high deductible)", Consumers' Research Magazine, vol. 76, No. 10, pp. 16. Oct. 1993.
Commununity Hearth Health Programs: Components, Ratio: John P. Elder, Thomas L. Schmid, Phyillis Dower and Sonja Hedlund; Journal of Public Health Policy; Palgrave Macmillian; 1993 winter; pp. 463-479.
Ferling, Rhona L.; "New Plans, New Policies" Time Insurance Co., Apr. 199; 93 12 ABI/INFORM Global (pp. 78-84).
Unumprovident (http://w3.unumprovident.com/enroll/elpasoisa/your_plan.htm; 2002.
Consumer-Driven Health Plans Catch on as Myths Fall by Wayside (Sep. 4). PR Newswire, 1.
Art Technology Group; Discovery Holdings to exploit online interest in healthcare and life assurance with ATG commerce functionality; Revenue potential significant as 70% of Discovery members access the internet. (Oct. 28). M2 Presswire, 1.
"Absenteeism Control"; Cole, Thomas C. et al; Management Decision; London: 1992. vol. 20, Iss. 2; p. 12 (AC).
Saleem, Haneefa: "Health Spending Accounts"; Dec. 19, 2003; posted online at http://www.bls.gov/opub/cwc/print/cm20031022ar01p1.htm.
Insure.com; "The lowdown on life insurance medical exams"; Jun. 28, 2006; Imaged from the Internet Archive Waybackmachine on May 10, 2006 at http://web.archive.org/web/20060628231712/http://articles.moneycentral.msn.com/Insurance/Insureyourlife/thelowdownonlifeinsurancwemedicalexams.aspx.
Definition of insurance, New Penguin Business Dictionary, Retreieved Oct. 26, 2008 from http://www.credoreference.com/entry/6892512/.
International Search Report for PCT/IB05/003842 filed Dec. 21, 2005 (WO2006/072822).
Written Opinion for PCT/IB05/003842 filed Dec. 21, 2005 (WO2006/072822).
International Preliminary Report on Patentability for PCT/IB05/003842 filed Dec. 21, 2005 (WO2006/072822).
International Search Report for PCT/IB07/051945 filed May 23, 2007 (WO2007/141695).
Written Opinion for PCT/IB07/051945 filed May 23, 2007 (WO2007/141695).
International Preliminary Report on Patentability for PCT/IB07/051945 filed May 23, 2007 (WO2007/141695).

International Search Report for PCT/IB07/051946 filed May 23, 2007 (WO2007/141696).
Written Opinion for PCT/IB07/051946 filed May 23, 2007 (WO2007/141696).
International Preliminary Report on Patentability for PCT/IB07/051946 filed May 23, 2007 (WO2007/141696).
International Search Report for PCT/IB07/051947 filed May 23, 2007 (WO2007/141697).
Written Opinion for PCT/IB07/051947 filed May 23, 2007 (WO2007/141697).
International Preliminary Report on Patentability for PCT/IB07/051947 filed May 23, 2007 (WO2007/141697).
International Search Report published Apr. 23, 2009 for PCT/IB071051948 filed May 23, 2007 (WO2007/141698).
Written Opinion published Mar. 13, 2009 PCT/IB07/051948 filed May 23, 2007 (WO2007/141698).
International Preliminary Report on Patentability published Mar. 17, 2009 for PCT/IB07/051948 filed May 23, 2007 (WO2007/141698).
International Search Report for PCT/IB07/053906 filed Sep. 26, 2007 (WO2008/038232).
Written Opinion for PCT/IB07/053906 filed Sep. 26, 2007 (WO2008/038232).
International Preliminary Report on Patentability for PCT/IB07/053906 filed Sep. 26, 2007 (WO2008/038232).
International Search Report for PCT/IB01/01406 filed Aug. 8, 2001 (WO2002/013438).
International Preliminary Report on Patentability for PCT/IB01/01406 filed Aug. 8, 2001 (WO2002/013438).
International Search Report for PCT/IB2007/053760 filed Sep. 18, 2007 (WO2008/035280).
Written Opinion for PCT/IB2007/053760 filed Sep. 18, 2007 (WO2008/035280).
International Preliminary Report on Patentability for PCT/IB2007/053760 filed Sep. 18, 2007 (WO2008/035280).
U.S. Appl. No. 10/344,176, Response to Office Action Nov. 9, 2009.
U.S. Appl. No. 10/819,256, filed Apr. 6, 2004.
U.S. Appl. No. 10/819,256, Final Rejection Jan. 6, 2009.
U.S. Appl. No. 10/819,256, Non-Final Rejection Mar. 18, 2008.
U.S. Appl. No. 10/819,256, Response to Office Action Sep. 18, 2008.
U.S. Appl. No. 11/097,947, filed Apr. 1, 2006.
U.S. Appl. No. 11/097,947, Non-Final Rejection Nov. 10, 2009.
U.S. Appl. No. 11/097,947, Final Rejection Jun. 7, 2010.
U.S. Appl. No. 11/097,947, Response to Office Action Mar. 10, 2010.
U.S. Appl. No. 10/818,574, filed Apr. 6, 2004.
U.S. Appl. No. 10/818,574, Non-Final Rejection Feb. 4, 2009.
U.S. Appl. No. 10/818,574, Response to Office Action May 4, 2009.
U.S. Appl. No. 11/074,453, filed Mar. 8, 2005.
U.S. Appl. No. 11/074,453, Non-Final Rejection Mar. 4, 2009.
U.S. Appl. No. 11/074,453, Requirement for Election Mar. 31, 2010.
U.S. Appl. No. 11/074,453, Notice of Non-compliant response Nov. 9, 2009.
U.S. Appl. No. 11/074,453, Response to Office Action Apr. 29, 2010.
U.S. Appl. No. 11/074,453, Response to Office Action Nov. 23, 2009.
U.S. Appl. No. 11/074,453, Response to Office Action Jul. 6, 2009.
U.S. Appl. No. 11/794,830, filed Jan. 22, 2008.
U.S. Appl. No. 11/794,830, Final Rejection Dec. 7, 2009.
U.S. Appl. No. 11/794,830, Non-Final Rejection May 27, 2009.
U.S. Appl. No. 11/794,830, Response to Office Action Sep. 28, 2009.
U.S. Appl. No. 11/794,830, Response to Office Action Apr. 7, 2010.
U.S. Appl. No. 11/903,607, filed Sep. 24, 2007.
U.S. Appl. No. 11/903,607, Final Rejection Jan. 28, 2010.
U.S. Appl. No. 11/903,607, Non-Final Rejection May 13, 2009.
U.S. Appl. No. 11/903,607, Response to Office Action Aug. 12, 2009.
U.S. Appl. No. 11/903,607, Response to Office Action Apr. 28, 2010.
U.S. Appl. No. 12/442,549, filed Mar. 24, 2009.
U.S. Appl. No. 12/477,179, filed Jun. 3, 2009.
U.S. Appl. No. 12/477,208, filed Jun. 3, 2009.
U.S. Appl. No. 12/477,213, filed Jun. 3, 2009.
U.S. Appl. No. 12/477,225, filed Jun. 3, 2009.
U.S. Appl. No. 12/477,189, filed Jun. 3, 2009.
U.S. Appl. No.12/721,619, filed Mar. 11, 2010.
U.S. Appl. No. 11/715,181, filed Mar. 7, 2007.
U.S. Appl. No. 11/715,181, Non-Final Rejection Nov. 3, 2009.
U.S. Appl. No. 11/715,181, Non-Final Rejection May 12, 2010.
U.S. Appl. No. 11/715,181, Response to Office Action Feb. 3, 2010.
U.S. Appl. No. 12/112,165, Final Office Action Feb. 10, 2011.
U.S. Appl. No. 12/477,225, Non-final Office Action Mar. 25, 2011.
U.S. Appl. No. 12/122,549, Non-final Office Action Mar. 30, 2011.
U.S. Appl. No. 12/333,465, Non-final Office Action Mar. 30, 2011.
U.S. Appl. No. 11/074,453, Response to final office action Dec. 20, 2010.
U.S. Appl. No. 11/715,181, Response to Office Action Mar. 11, 2011.
U.S. Appl. No. 12/912,009, co-pending application filedOct. 26, 2010.
U.S. Appl. No. 12/912,040, co-pending application filed Oct. 26, 2010.
u1—Discovery Life "The Discovery life Portfolio", 62 pgs—2008.
u2—AFLAC "Personal Disability Income Protector", 6 pgs—Jul. 2003.
v1—Discovery Life—"Discovery life Group Risk LIFE PLAN".
v1—Discovery Life—"Why Discovery Life"—4 pgs—May 29, 2008.
v2 GE Group Life Assurance Company—Group Short Term Disability Insurance—18 pgs, Oct. 29, 2004.
w1 Wenfin Financial Services, "Discovery Life Plan" www.bmlink.co.za/WenFininsurance—Website download, 58 pgs, Aug. 5, 2011.
w2 EconEdLink—"How Long is Your life?"—Tutorial from EconEdLink.com web-site, 4 pgs, posted Sep. 13, 2004.
x1 AFLAC—"Personal Cancer Indemnity Plan" Level 3, 11 pgs, Jun. 2005.
x2 Gendell Murray, "Retirement age Declines again in 1990s", Monthly Labor Review, 10 pgs, Oct. 2001.
u1—Discovery Life "Benefit version Reference Guide" Oct. 2008.
w1 WenfinWebPages for Discovery Life Nov. 13, 2006.
w HLC Financial Services, Discovery News Feb. 2009.
x1 AFLAC—Discovery Life "Application for Discovery Card Protector" Nov. 2007.
u2—Discovery Life "The Disovery Life Portfolio" Nov. 20, 2008.
w2 Discovery Life "Discovery Individual LIE PLAN Guide" Aug. 4, 2009 EconEdLink—How Long is Your life?—Tutorial from EconEdLink.com web-site, posted Sep. 13, 2004.
x2 Discovery Life "The Discovery Life Portfolio" Jun. 2008.
u3 Discovery Invest Group Retirement {Plan Financial Solutions for employees: Oct. 17, 2009.
U—ATG Customer Success Story: Discovery Heathly 2006 ART Tech Group, Inc.
V Discovery Vitality; Discovery Vitality 2009 Sep. 12, 2008.
W Discovery Invest, Group Retirement Plan Finanical solutions for employees Jan. 17, 2009.
X Baker et al. Pay for Performance Incentive Programs in Healthcare; Market Dynammics and Business Process-Research Report 2003.
u PruHealth, Individual Policy Document Jul. 2008.
v Discovery Vitality, Lesson Plans Grade 4 and 5 Apr. 2, 2008.
U The Discovery Life, "Technical guide for financial advisers" Nov. 2008.
U.S. Appl. No. 12/122,549, RCE response Jan. 6, 2012.
U.S. Appl. No. 12/441,447, Final Office Action Jan. 10, 2012.
U.S. Appl. No. 12/441,447, Response filed Nov. 1, 2011.
U.S. Appl. No. 11/794830, Non-Final Rejection Dec. 19, 2011.
U.S. Appl. No. 11/903,607, Office Action Nov. 30, 2011.
U.S. Appl. No. 12/477,189 Preliminary Amendment filed Nov. 4, 2011.
U.S. Appl. No. 12/477189 Final Office Action Dec. 5, 2011.
U.S. Appl. No. 12/721,619, Preliminary Amendment filed Nov. 3, 2011.
U.S. Appl. No. 12/912,009 Non-final Office Action Dec. 19, 2011.
U.S. Appl. No. 13/318,620, filed Nov. 3, 2011.
U.S. Appl. No. 13/386,431 filed Jan. 23, 2012.
International Search Report dated Nov. 2, 2011 for PCT/IB11/51627 (W02011/128873).

* cited by examiner

Bonus Calculation Module

Step 1. Premiums

A – Send message to Premium Subsystem
B – Send Message to Membership Subsystem

DATA PROCESSING SYSTEM FOR ACCURATELY CALCULATING A POLICYHOLDER'S DISCOUNT IN A MEDICAL INSURANCE PLAN AND A METHOD THEREFOR

BACKGROUND OF THE INVENTION

This invention relates to a data processing system for accurately calculating a policyholder's discount in a medical insurance plan and to a method therefor.

Good management of a medical insurance plan, typically a private medical insurance plan, is obviously important to the plan managers to ensure the ongoing financial viability of the plan. However, in recent years, in some countries, there has been a change in the management of a medical insurance plan to focus on the policyholders of the plan and to encourage the policyholders of the plan to stay healthy. To date, this has not been a discernible trend in the United Kingdom.

Examples of the developments in this area are described in South African patents numbers 99/1746 and 2001/3936, the contents of which are incorporated herein by reference.

Another method of managing a medical insurance plan that is focused on encouraging the policyholders of the plan to manage their claims is to offer the policyholders a discount based on the mount of premiums paid to the medical insurance plan, the amount of claims made from the medical insurance plan and possibly the level of the policyholder in an incentive scheme associated with the insurance plan. This approach addresses two latent problems inhering in insurance in general, namely moral hazard, whereby policyholders may be incentivised to claim and adverse selection, whereby high-risk individuals are attracted to purchase the insurance plan. In addition, the approach mitigates the tendency in private medical insurance to reward sickness.

However, the practical implementation of such a method poses technical difficulties as it is not simple to determine the amount of premiums paid to the medical insurance plan and the amount of claims made from the medical insurance plan. This is because the amount of premiums paid can change suddenly if a policyholder changes their plan options, for example. Also, the amount of claims made can vary if there are claims which have been submitted but have not yet been processed or if there are claims which are under dispute, for example. Simply to take a snapshot of how much premiums has been paid in a given period and how many claims have been paid out to the policyholder would not give accurate amounts for use in determining an appropriate discount.

The present invention provides a data and rules processing system for accurately calculating a policyholder's discount in a medical insurance plan and to a method therefor.

SUMMARY OF THE INVENTION

According to one embodiment of the invention there is provided a data processing system for accurately calculating a discount in a medical insurance plan, the system comprising:
a premiums module adapted to access data regarding the amount of premiums paid by a policyholder of the medical insurance plan for a predetermined period,
a claims module adapted to access data regarding the amount of claims paid by the medical insurance plan to the policyholder for the predetermined period, the claims module being further adapted to access data to determine if there have been any claims submitted by a policyholder which have not yet been paid, and if so to apply a set of rules to each submitted claim which has not been paid to determine if it is likely to be paid, and if the claim is likely to be paid then adding the amount of the claim to the amount of claims already paid for the predetermined period; and
a discount module adapted to receive data from the premiums module and the claims module and to use the data to calculate a discount amount.

In another embodiment a machine-readable medium comprising instructions, which when executed by a machine, cause the machine to perform a method of calculating a discount in a medical insurance plan, the method comprising:
accessing premiums data regarding the amount of premiums paid by a policyholder of the medical insurance plan for a predetermined period,
accessing claims data regarding the amount of claims paid by the medical insurance plan to the policyholder for the predetermined period;
accessing further claims data to determine if there have been any claims submitted by a policyholder which have not yet been paid, and if so to apply a set of rules to each submitted claim which has not been paid to determine if it is likely to be paid, and if the claim is likely to be paid then adding the amount of the claim to the amount of claims already paid for the predetermined period; and
using the data accessed to calculate a discount amount.

In a further embodiment a method of calculating a discount in a medical insurance plan, the method comprising:
accessing premiums data regarding the amount of premiums paid by a policyholder of the medical insurance plan for a predetermined period,
accessing claims data regarding the amount of claims paid by the medical insurance plan to the policyholder for the predetermined period;
accessing further claims data to determine if there have been any claims submitted by a policyholder which have not yet been paid, and if so to apply a set of rules to each submitted claim which has not been paid to determine if it is likely to be paid, and if the claim is likely to be paid then adding the amount of the claim to the amount of claims already paid for the predetermined period; and
using the data accessed to calculate a discount amount.

DESCRIPTION OF PREFERRED EMBODIMENTS

Referring to South African patents numbers 99/1746 and 2001/3936, the contents of which are incorporated herein by reference, these documents describe a method of managing a medical insurance plan wherein a plurality of health-related facilities and or services are offered to policyholders of the medical insurance plan. The patents list a number of health-related facilities and/or services, examples of which are an approved health club or gymnasium, a weight-loss programme or a smoke ender programme. Use of the facilities and/or services by policyholders is monitored and points are awarded to a policyholder for using the facilities and/or services. The following table summarises examples of points-earning activities:

| Category | Detailed category/activity | Eligibility | Points awarded | Frequency |
|---|---|---|---|---|
| Fitness | Gym workout | Any | 5 | per workout |
| | Fitness assessment | Any | 75 | per assessment |
| | Organised fitness event | Any | 20 | per event |
| Healthy choices | Being a non-smoker | Any | 250 | per year declaration made |
| | If a smoker, joining a smoke-ender program | Any | 150 | per event |
| | Reading self help articles | Any | 10 | per article |
| | Online risk assessment | Any | 25 | per assessment |
| | Completing a first aid course | Any | 30 | points earned in each of the two years |
| | Passing an online health information quiz | Any | 40 | per event |
| | Stress centre | Any | 25 | per assessment |
| Preventative measures | Regular checkups for child, baby | <12 years | 250 | per event |
| | Completed vaccinations | <24 months | 200 | per event |
| | Mammogram | women >45 years | 250 | per event |
| | Glaucoma testing | >40 years | 250 | points in each of the two years |
| | Glucose testing | >40 years | 250 | points in each of the two years |
| | Dental checkups | Any | 150 | per event |
| | Pap smears | women >16 years | 250 | per event |
| | Cholesterol screening | men >35, women >45 | 250 | points in each of the five years |
| | Prostate screening | men >50 | 250 | per event |
| | Use online/telephone GP | Any | 20 | per event |
| | Flu vaccination | Any | 150 | per event |
| Nutrition | Online nutrition articles | Any | 10 | per article |
| | Creating healthy meal plan online | Any | 30 | per event |
| Results | Maintaining fitness rating | Any | 30 | per level maintained |
| | Improving fitness rating | Any | 50 | per level improved |
| | Maintaining target BMI band | Any | 30 | per level maintained |
| | Improving target BMI band | Any | 50 | per level improved |
| | Maintaining body fat target | Any | 30 | per level maintained |
| | Improving body fat target | Any | 50 | per level improved |
| | Maintaining blood pressure | Any | 30 | per level maintained |
| | Improving blood pressure | Any | 50 | per level improved |
| | No sick days off work bonus | Any | 200 | per year achieved |
| | Carryovers | | | |
| | Total points end of second year | | | |
| | ... third | | 10% | |
| | ... fourth | | 15% | |
| | ... fifth+ | | 20% | |

Further, as described in these patents, a plurality of status levels in an incentive scheme are defined which are described in these patents as blue, bronze, silver and gold. Depending on the number of points a policyholder is awarded, one of these status levels are allocated to the policyholder so that the policyholder's status level is essentially according to the use of the facilities and or services.

Finally, a reward is allocated to the policyholders depending on their status level. However, the rewards contemplated in these patents do not always motivate policyholders.

Premiums for most medical insurance plans rise each year to keep pace with inflation and this is irrespective of whether or not the policyholder claims from the medical insurance plan. Thus, another method of motivating policyholders would be to provide the policyholder's with a discount which either takes the form of a cash-back bonus or of a decrease in the premiums payable for the medical insurance plan for a future period of time.

According to the present invention, the amount of claims from the medical insurance plan that a policyholder makes, together with the policyholder's status level in the incentive scheme are used to determine the policyholder's premium payable in the coming year.

Figure 1:
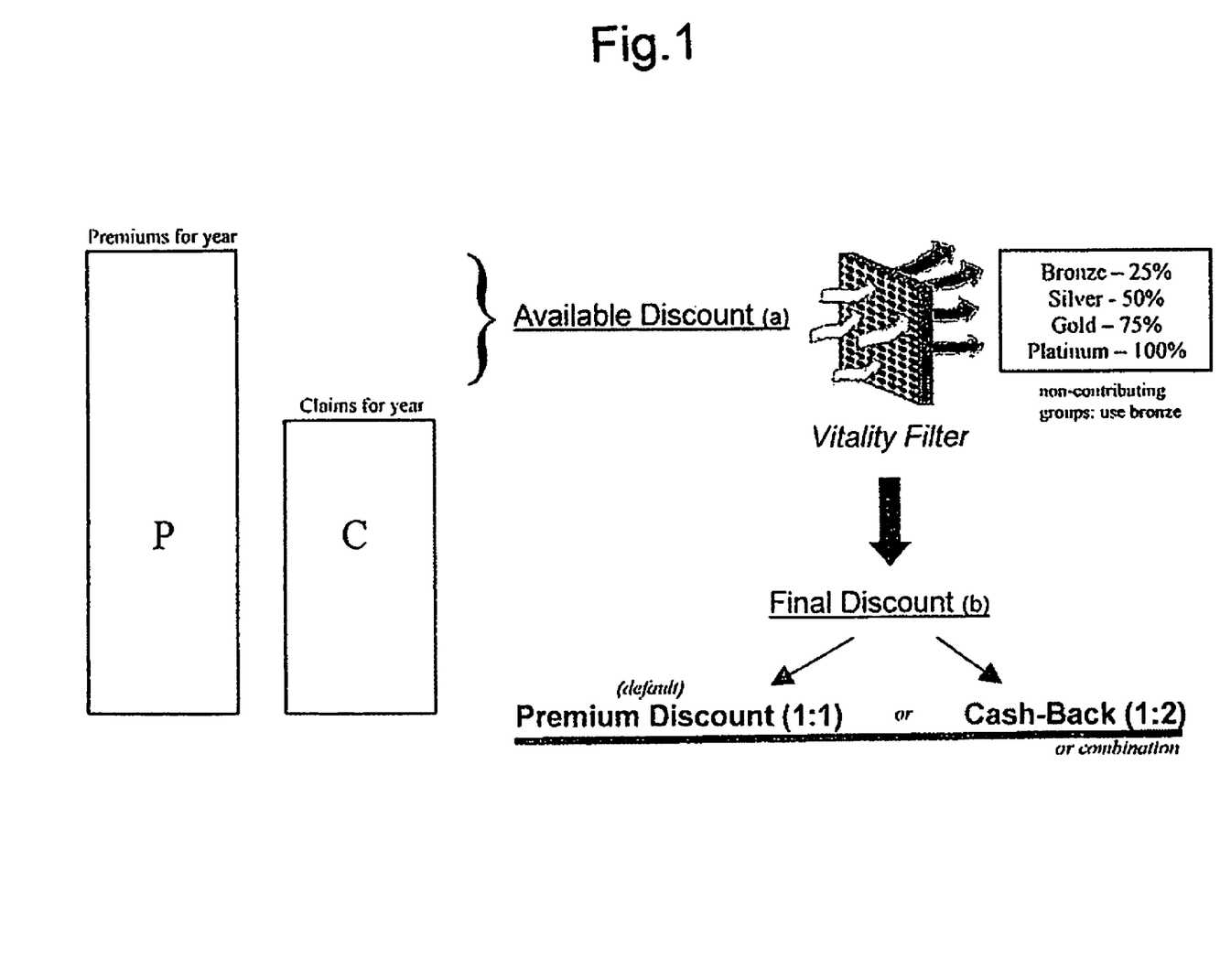
FIG. 1 is a schematic representation of a discount methodology in a medical insurance scheme.

For example, referring to FIG. 1, a married man aged 36 living in London covering his spouse and two children could expect to pay about £80 per month. That's p=£960 in a full year. If we assume he claims £428 during the year for private consultations, that means the amount potentially available as a discount off next year's premium, is £532 (£672-£428).

If the incentive scheme is also used then the actual percentage of the £532 that is applied as a discount from the following year's premium depends on how actively the policyholder looked after their health. From a minimum of 25% right up to the full £532. Thus a full 100% of the amount could be applied to reduce the subsequent year's premium. Alternatively, the policyholder can take 50% of the discount in cash.

In this scenario, whether its nearer the 25% or the 100% discount level depends entirely on the policyholder's status. Everyone starts as a Bronze policyholder and even if they do not do anything further to improve their health they will always be entitled to the Bronze policyholder discount rate of 25%. So in the example above a policyholder would always qualify for £133 off the following year's premium. But with a little effort a policyholder could enjoy Gold or Platinum status with discounts of up to 100% as can be seen from the exemplary table below:

| | Discount rate (%) | Points required |
|---|---|---|
| Bronze | 35 | Nil |
| Silver | 50 | 1500 |
| Gold | 75 | 2500 |
| Platinum | 100 | 3200 |

In essence, the method of managing a medical insurance plan described above is focused on the policyholder and incentivises the policyholder to look after their health.

In order to implement the abovementioned method, it is necessary to provide a data processing system which is able to calculate the discount.

However, the practical implementation of such a method poses technical difficulties as it is difficult to determine the amount of premiums paid to the medical insurance plan and the amount of claims made from the medical insurance plan. This is because the amount of premiums paid can change suddenly if a policyholder changes their plan options, for example. Also, the amount of claims made can vary if there are claims which have been submitted but have not yet been processed or if there are claims which are under dispute, for example. Simply to take a snapshot of how much premiums have been paid in a given period and how many claims have been paid out to the policyholder would not give accurate amounts for use in determining an appropriate discount.

The present invention is implemented in a machine in the exemplary form of a computer system within which a set of instructions, for causing the machine to perform the methodology of the present invention. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer or any machine capable of executing a set of instructions (sequential or otherwise) that specify actions to be taken by that machine. Further, while only a single machine may be referred to below, the term "machine" shall also be taken to include any collection of machines that individually or jointly execute a set (or multiple sets) of instructions to perform any one or more of the methodologies discussed herein.

The exemplary computer system will typically includes a processor (e.g. a central processing unit (CPU) a graphics processing unit (GPU) or both), a main memory and a static memory, which communicate with each other via a bus. The computer system may further include a video display unit (e.g. a liquid crystal display (LCD) or a cathode ray tube (CRT)). The computer system also includes an alphanumeric input device (e.g., a keyboard), a cursor control device (e.g. a mouse), a disk drive unit, a signal generation device (e.g. a speaker) and a network interface device.

The disk drive unit includes a machine-readable medium on which is stored one or more sets of instructions (e.g. software) embodying any one or more of the methodologies or functions described herein. The software may also reside, completely or at least partially, within the main memory and/or within the processor during execution thereof by the computer system, the main memory and the processor also constituting machine-readable media.

The software may further be transmitted or received over a network via the network interface device.

While the machine-readable medium is shown in an exemplary embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. The term "machine-readable medium" shall accordingly be taken to include, but not be limited to, solid-state memories, optical and magnetic media, and carrier wave signals.

Figure 2:
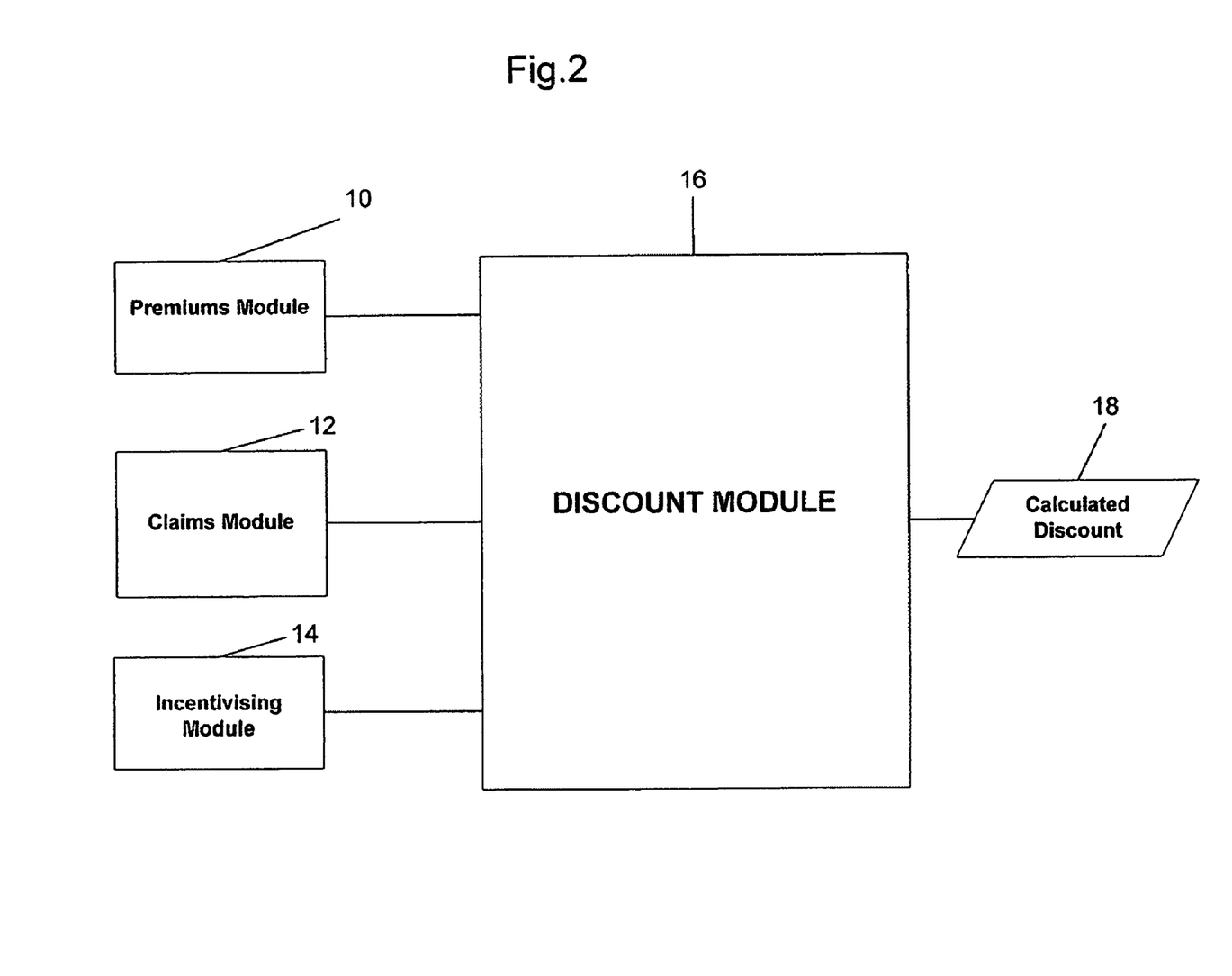
FIG. 2 is a schematic representation of a system according to the present invention used to implement the discount methodology illustrated in FIG. 1.

Referring to FIG. 2, the machine implemented present invention includes a premiums module 10, a claims module 12 and possibly an incentive module 14. All of these are operatively connected to a discount module 16 which calculates the calculated discount 18.

Furthermore, the abovementioned modules may form part of a larger system which implements the medical insurance plan.

Referring first to the premiums module, it will be appreciated that the premiums paid could be calculated for any predetermined period, for example monthly, quarterly, biannually or annually. It is envisaged that in a preferred embodiment, the premiums payable will be calculated annually. In this case, the prior predetermined period will be the previous year.

The premium on a policy is calculated when it is first created. Additionally, a recalculation occurs for certain subsequent changes to the policy. The premium calculation will generate a change in the premium based on the effective date of the administration change.

Additional complexities arise in the context of insurance plans sold to a group of individuals through their employer. Such plans differ in premiums and applicable benefits compared plans sold to an individual. A key feature of administration in these cases is to provide employers with an option of covering only a portion of a policyholder's insurance contribution, also known as "split" or "flexible" billing. This is essentially a means of splitting the premium for each policyholder between employer and employee as a fixed percentage, or some other mathematical function. The split may also be based on the policyholder's dependants, with the employer opting to cover a percentage of the relevant premium/s. Additionally, employers may pay for cover under a certain plan, leaving the employee to upgrade if they desire, and to pay the difference. Either way, premiums paid by the employee are deducted from salary by the employer where the employer may receive a discretionary discount as a result of performing this collection function. All records of such transactions are accounted for within the calculation system.

The premiums module 16 is designed to "split" the overall premium into portions for the various paying parties, such as the policyholder portion, employer portion etc. This calculation is based on a combination of data and rules in accordance with the above description. These rules are summarized below:

1) The calculation ascertains the billing category and benefit plan being referenced from policyholder data. An additional rule determines the subsequent action sequence based on possible permutations of this data
2) Each step is then processed in the order paying party, premium component, split sequence
3) The step is applied to each premium amount of the same component, applied to premium amounts of the same type for each dependent
4) The split amount is calculated according to the rule definition as set up for the specific employer. This could simply be a user specified amount, or a percentage of this premium amount or more complex types like table look ups, carried over values etc.
5) Based on the hierarchy defined for each component, the dependant amount types for the same component and party are calculated. Their split amount for this party is calculated in the same ratio as in the as for the principal policyholder
6) For the "parents" of premium sub-components, each amount calculated is added to a running total, so that the rule that the parents amount equals the sum of the child amounts for the same party is enforced.

Generic Definition of Premium Components

The core of the premium calculation function rests within data and systems, and is designed to furnish real-time individual and cumulative premium contributions for a given period. Rates tables are stored and referenced to determine the applicable rate for the policyholder for whom the calculation has been invoked. These premium rates are determined according to various policyholder choices, including:
1) Plan choice
2) Age of the policyholder
3) Status of the policyholder
4) Smoker/non-smoker status
5) Hospital accommodation grade
6) Location of hospital (inside/outside London)

A risk factor is then incorporated to this premium rate based once again on policyholder choice such as excess level, grade of hospital accommodation etc. The calculation of this risk factor may result in a risk loading onto the premium rates determined above. The newly adjusted premium amount is then also subject to additional premium loadings such as insurance premium tax. Each of these loadings will be stored as their own separate components in the premium breakdown, so that they can be disclosed separately where needed. All of the above is stored and calculated automatically based on choices made by the policyholder as an input into the new business application process. Changes to any of the above components can be done effective any day of the month and thus premiums can change based on an 'any-date' basis.

The flexibility of the design extends to a means of specifying generic types of premium component such as "risk premium", "administration fee", "expense allowance". Subcomponents may be generated according to the templates for each parent type. The Low claims Bonus is configured to either include or exclude various component types from its premium calculations.

Referring now to the calculation of the claims amount, since there are many steps in processing claims from receipt through to resolution, the system of the medical insurance plan is predicated on obtaining identification of a claim as soon as it has been received. The tasks of capturing the claims is thus split into "header capture" phase and "line capture" phase with the former allowing tracking of claims processing to proceed even though not all data has been electronically captured.

The medical insurance system also contains modules to render claims into a standard captured format. This enables claims to be identified as soon as possible regardless of receipt method. A claim may be received through mail, email. Fax, hand-delivery or electronically.

The system has been designed to automatically insert the image of a claim into a workflow pipeline. In order to do this, a context for the claim must first be derived. Since all claims require pre-authorisation, the goal of this step is to find the corresponding authorisation data, and to perform a series of automated data comparisons. At authorisation time the following data will have been obtained from a notifying party: identification of policyholder, identification of clinical consultant or hospital, set of clinical codes representing the clinical criteria against which authorisation is granted, and the expected dates and times of clinical treatments. (In complex cases this data may be modified subsequent to authorisation as a function of case management and other communications).

The contextualisation of the claim is then a means of matching data on that claim with a pre-existing data set. In many cases, this match will not be exact, and a series of rules is required to automatically perform the association. These rules are based on the following set of criteria:

A clinical code does not match the expected set of codes, but may still be valid for a number of reasons (the code could be clinically similar, or may be coded in diagnosis—rather than procedure-format)

The service provider may in some way be affiliated to the expected provider: e.g. same hospital group, or doctors who work both individually and in partnership Identifiers of policyholders and doctors could be incorrect or incomplete Cases like these may be automatically or partially resolved based on the firing of a series of rules within the rule base.

In other cases, a separate set of rules may be applied instead: for example, the clinical codes may be missing, but the claim may be on a case basis only. The system will perform this and other checks in order to determine if the case claim can proceed despite missing data. In all cases there is a defined minimal data set without which the claim cannot be contextualised.

If none of the rules are able to perform the association categorically, the system can route the claim to a party capable of performing this association.

Immediate adjudication on a captured claim is subject to a wide number of rules incorporated into the system's data and algorithms. The schematic below shows the adjudication rules within the context of the overall claims pipeline.

A formatted text version of the invoice is captured from an image of the original invoice. Details captured include the provider, policyholder, service dates, procedures and claimed amounts.

The following is then checked for:
1. Provider is registered, active and has not been marked for fraud.
2. Membership and dependant exists, is not suspended.
3. Procedure codes exist and are appropriate for the billing provider If the service date falls within the admission and discharge dates of an approved hospitalisation for a particular dependent, the invoice is linked to the event.

The maximum tariff and the agreed/standard tariff are determined per line of the invoice. Rules concerning how much to pay are always with reference to these maxima and tariff rates. The tariff calculation is influenced by factors such as the procedure done, the provider and his network agreements.

The system checks that the invoice has not been paid previously, before funding the current invoice. The criteria for deciding that a line of the invoice is a true duplicate of a previously paid line currently varies per medical specialty. For example, the procedure code, provider, policyholder, dependant and service date must all match across two GP invoice lines before they are considered to be true duplicates, but for pathology invoices, the dependant number is not relevant. True duplicates are rejected automatically.

Invoice lines are rejected if clinical billing rules are violated within an invoice. For example there may be two pathology procedure codes. One procedure code is for a set of tests, while the second procedure code is for a particular test that is included in the set of tests under the first procedure code. It is incorrect for the provider to bill both procedures on an invoice.

When a policyholder joins, an underwriting process may determine that cover is excluded for certain conditions for a certain period of time. For example, a general policyholder-specific underwriting exclusion can exclude all cover for two years. If a policyholder has a pre-existing condition such as diabetes, a condition-specific exclusion can be applied for a period of time. All invoices relating to an underwritten condition are not paid. In such cases, the routing algorithm will decide on whether to ensure human verification is obtained. Alternatively, "moratorium" underwriting may be used whereby no investigation is performed up-front, but deferred until such time as the policyholder presents with a clinical condition. The normal underwriting process will then ensue at the later time.

There are rules for non payment of invoices, that are proprietary to the product. These rules can be clinical decisions or benefit decisions from the business or risk management owners of the product. For example, day to day dentistry and infertility treatment are not covered. The rules are defined in terms of plans, procedure codes or categories, medicine codes, providers, practice types, age ranges etc. These rules are all ultimately an intrinsic part of the system. Where there are product rules coded in terms of clinical codes, the system will add a warning reason code to an invoice line for an excluded procedure. The system will not reject the invoice line as a product exclusion unless the decision is endorsed by an assessor.

The amount paid on an invoice line can be constrained by limits. The applicable limit towards which an invoice line will accumulate, will be identified by the procedure code, practice type or event admission category.

If the policyholder selected an annual excess, then the system will not pay invoices to the value of the excess amount per dependant. Accumulation to the excess amount will be according to the order in which the invoices are received. This rule is may be automatically overwritten in certain circumstances. The amount which would have paid will be accumulated towards the excess i.e. not necessarily the full claimed amount, and not invoices that would never have been covered by the plan.

If the policyholder has selected a plan that has deductibles for specific in-hospital procedures, then the deductible amount will not be paid on the hospital invoice corresponding to the event approved for the specific procedure.

Policyholders or employers can have payment of their invoices suspended for reasons such as non payment of premiums or fraud. The status of the claim within the pipeline will be automatically updated.

An invoice that is received more than 3 months after the treatment took place is considered to have been submitted too late for payment.

A list of hospitals that are considered to be "In Network" will be published. The In-Network hospitals will include a selection of hospitals both inside and outside of London. When a policyholder takes out the policy, he or she can choose whether or not to include London hospitals in their list of In-Network hospitals. If a policyholder is admitted to an Out of Network hospital (either a London hospital when this option was not selected, or a hospital that is not on the Prudential Health list), there will be a co-payment applicable to the hospital account. £400 per day at an Out of Network hospital will be paid. Other co-payment options include: a 30% co-payment, a deductible on the event or payment of the equivalent of the cost of the hospitalisation had it taken place In Network. These rules are coded in the rule base.

The policyholder can select from several accommodation grade. Essential grade is a standard private hospital bed. Premier refers to more up market hospitals or better rooms in standard hospitals. Not all hospitals offer both accommodation grades, so a policyholder's choice of In Network hospital can be limited by their accommodation grade choice. A policyholder will have a per day rate paid in accordance with their accommodation grade choice, irrespective of which accommodation grade was actually used.

If the policyholder chooses to have treatment in a non-private NHS facility and the treatment would have been covered by their plan, then the policyholder is entitled to an NHS cash benefit. The NHS discharge form will be treated as a submitted invoice and a per day rate will be paid to the policyholder.

An approved hospital authorisation is a guarantee of payment. A set of meta-rules is embedded in the rules logic to resolve conflicts for claims that are guaranteed, but that violate other criteria.

The service provider or hospital is always paid, unless there is an indication on the invoice that the policyholder has already paid, in which case the policyholder is refunded.

The claims Adjudication system will check whether it is appropriate to route an invoice for Manual Assessment. Meta-rules determine if a previous rule application may be taken as binding, or if a warning alone should be applied and the claim routed for manual assessment. The workflow system will move claims to the Manual Assessment pool where appropriate.

Figure 3:
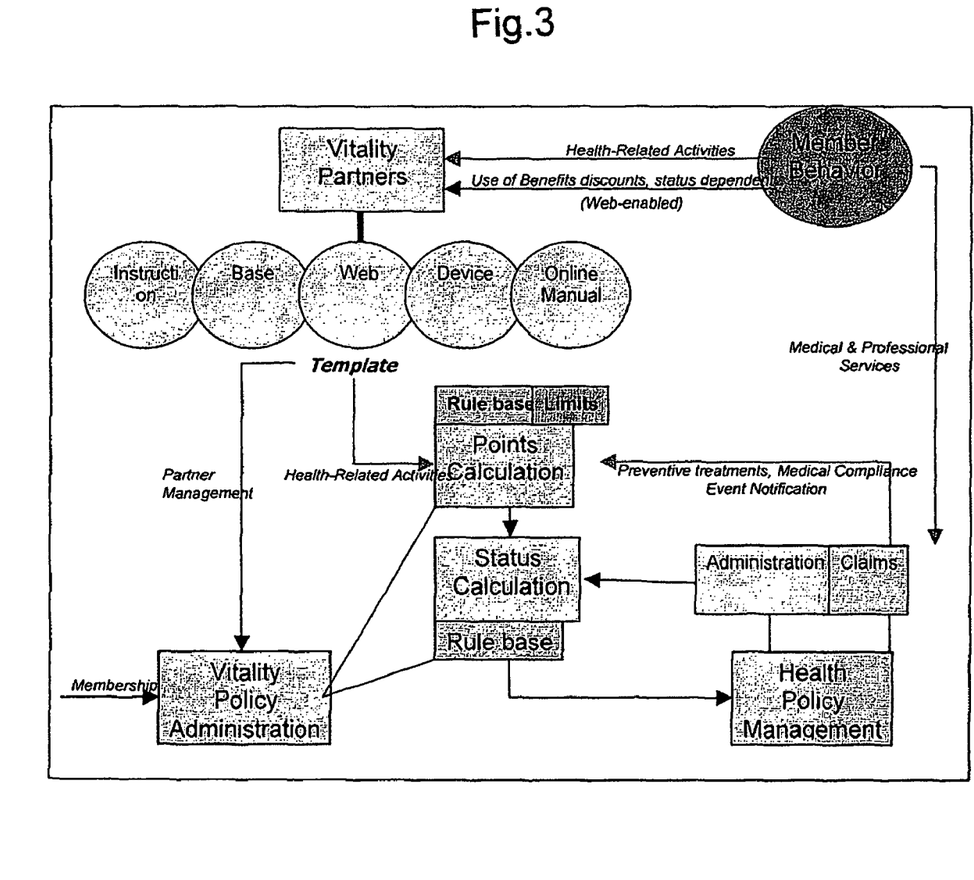
FIG. 3 is a schematic representation of an incentive system used together with a medical insurance scheme.

FIG. 3 illustrates the interconnecting aspects of software modules that combine to perform tasks associated with points and status allocations in an incentive programme. The programme will herein after be referred to as the Vitality™ programme.

Vitality partners may be split into those providing a health-related service (yielding points) or benefit partners providing goods or services to a Vitality policyholder at preferential rates. A given partner may fall into both categories.

Benefits-only partners normally communicate with administration systems at the financial level only, and have no bearing on Vitality points. The Vitality (section of the Health carrier) website facilitates communication with these partners allowing policyholders to redeem benefits. This could take place at retail point of sale, over the phone, or electronically in a "webmall" environment.

Some partners provide a health-related service to a policyholder, in which case the policyholder is in a points-accumulating position. Others provide access to goods and services at preferential rates dependant on a status level achieved through points-accumulating activities. In all cases, data transfer takes place between the Vitality Management System and the partner system, depending on requirements of the contract as well as the technical capabilities of the partner.

To cater for multiple scenarios, the Vitality System Software provides a set of five distinct communication templates to facilitate data exchange with various partners. Communication with a new partner can thus be implemented without additional development or integration, simply by application of an appropriate software module and communication protocol. The various methodologies are described below:

1. Base Exchange Protocol—This is used when a Vitality partner requires constant access to the comprehensive details of the entire Vitality policyholder base. The protocol uses mechanisms to ensure data currency as well as to minimise data volumes. Additional algorithms ensure the timely rectification of transmission errors, thus ensuring total data availability at point of transaction, usually a sign-up to a particular service.
2. Instruction Exchange Protocol—This is used when the entire data set is not required, but when detailed instructions for a set of actions to occur are transmitted on a need-to-know basis. This will occur for example when a policyholder registers for a particular service without any advance warning. The heart of the protocol is a mechanism reducing complex (possibly overlapping and contradicting) instructions into a single unified transmission message. This in turn makes use of a rules engine which makes use of specialised rules capable of expressing a variety of core and boundary conditions.

3. Web Services Protocol—This involves the modification of the partner systems to interface directly to a host web server. Relevant transaction data is transmitted using pre-built algorithms without the user of the partner software being directly aware of this. These algorithms make use of highly componentised code which is easily customisable to the needs of individual data exchange agreements.
4. Modem Device Protocol—If partner systems are not configurable to a web services protocol (or no systems exist), use may be made of a specialised hardware device. This device is activated (normally by a retail partner) to transmit transaction data and usage information to the Vitality host system. A modem linking the device with the prevailing telephone network is used in such an instance. The applicable receiving software module will translate and store data that arrives through this channel.
5. Online Protocol—In cases of fairly low transaction volumes, and failing integration into an existing partner system, data exchange is facilitated by a partner-specific website. The partner (securely) logs into the site and transmits all relevant data through interaction with a specialised user interface. This interface will make use of re-usable software components expressly designed for this purpose.

Points may be earned by virtue of communication from participating partners, or through direct communication with the policyholder via manual, telephonic or other electronic means. The relevant claims data will reside in the databases of the claims Management System. The onus is on that system to notify the Vitality points calculation module of a medical service which may be relevant (the arbiters of relevance are rules fired within the points calculation module).

The claims module will typically poll its data at predefined intervals and transmit the occurrence of a particular medical service (designated by a service code) to the Vitality modules. The polling program is a high-speed optimised module.

Points are allocated based on data received from partners through one of the protocols described above. Frequency of calculation is a function of stated service levels, constrained only by the time required to ensure error-free transmissions. In many cases points are allocated as soon as processing and verifying of an incoming transaction takes place.

Points-allocation is based on a set of generic user-driven data tables specifying the number of points associated with a particular activity. A supplemental rules engine is used to implement more complicated rules as well as for meta-rules.

Examples of complex rule formulations: 5000 points allowable for cholesterol tests only once in a three-year period; 2 fitness assessments allowed per year at five-month intervals; Membership to gym cancelled if less than 10 workouts in 3 months. Complex rules such as these are implemented in the rules base by means of Java "strategies". These are self-testing components which insert easily into any surrounding rules infrastructure.

A subset of the rules strategy is a three-tiered limits engine, which ensures that allocation of points cannot exceed pre-defined thresholds and sub-thresholds.

The primary determinant of Vitality status (e.g. "bronze", "silver", "gold", "platinum") is the number of points accrued within a policyholder portfolio. This may however be subject to the imposition of a number of rules implied by the Vitality contract itself, as well as the rules that inhere in the associated private medical insurance policy.

A Java rules engine implements these rules, which are extendable at multiple levels, right down to individual policyholder rules. This means that a new rule can be set up to cover the entire policyholder population, a set of employers (industry type, say), individual employers, individual policyholders, or even dependants of individuals.

This mechanism also allows the imposition of special rules for a group. For example a particular set of policyholders (e.g. those suffering from a particular chronic illness) may be awarded a higher Vitality level by the addition of an applicable rule or meta-rule.

Ideally, the low claims bonus should be done on precisely the renewal date of the policy. However, this is not possible for two reasons: firstly, some communication with the policyholder must take place in order for that policyholder to articulate benefit preferences accruing from the bonus; secondly, a "cut off" time prior to renewal must be imposed to allow the software to make the required calculations. It is desirable for this cut-off point to be as close to actual renewal as possible, to ensure that the policyholder is credited with maximum points, that all claims have been received, and that any premium adjustments are included in the calculation.

To ensure that a usable approximation is reached, a "snapshot" of all claims, points and premium activity is required from the calculation module. This module send messages to modules corresponding to these three sub-systems, and requests an immediate status check on all three operators for use in the bonus calculation.

The paragraphs below delve further into the functions performed by the calculation module 16. This module controls all necessary activities required to obtain relevant information from related sub-systems in the correct sequence.

The calculation module makes use of a "workflow" sequence that calls functions within the surrounding systems to obtain the necessary values for use in the discount formula. It uses these values, combined with the application of a built-in intelligence to compute the new premium. These steps are outlined below with reference to FIGS. 4a-4c:

Get Premiums

Figure 4A:
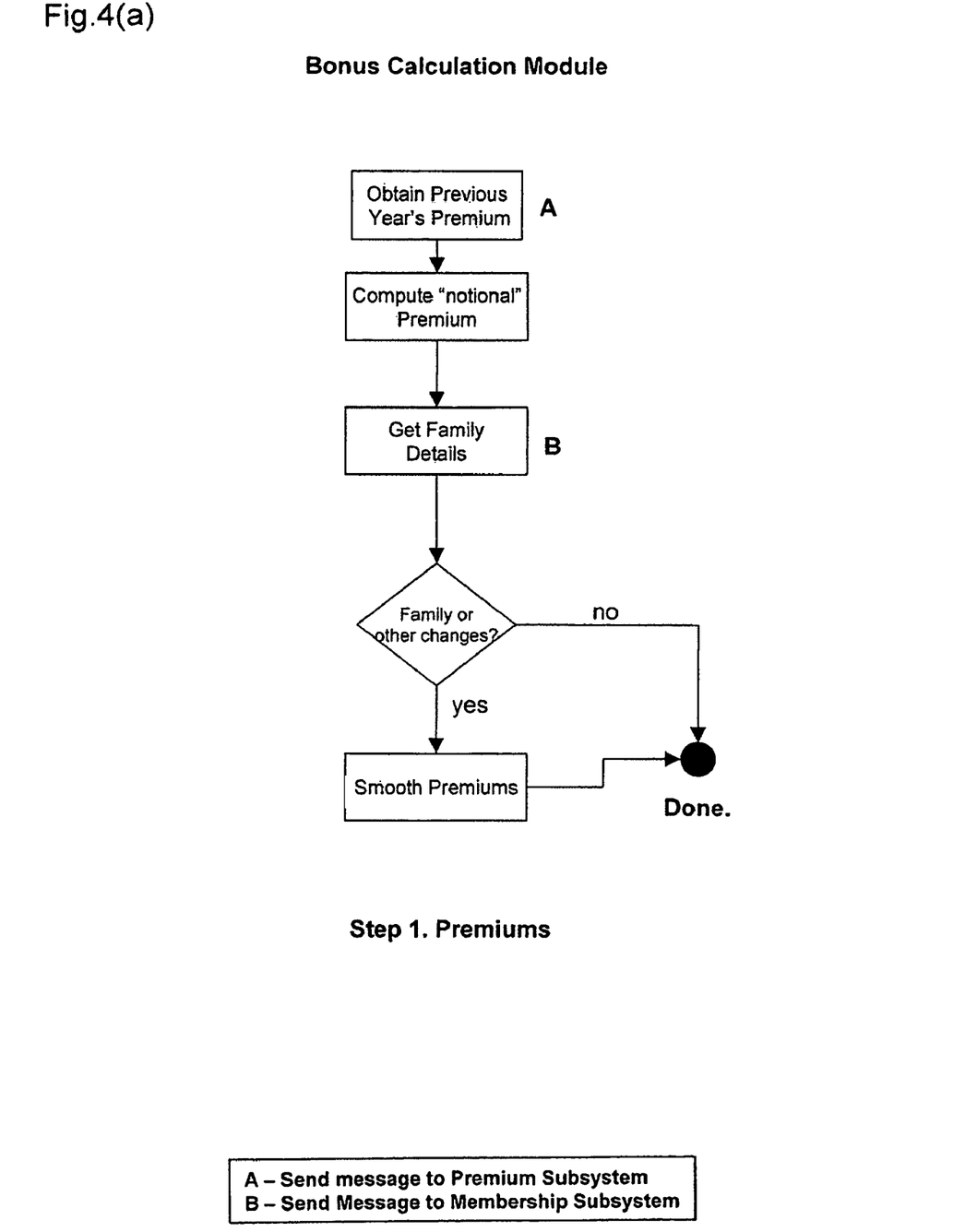
FIGS. 4(a), 4(b) and 4(c) is are a schematic representation of the actions taken by a discount calculation program to obtain data from various sources required to perform the calculation.

The bonus calculation module sends a message to the premium system. It obtains a sum of all premiums paid since the last such calculation was performed. It then performs certain checks on the returned value in order to address the following:

Ensure "notional" premium is used to determine value for calculation. This is relevant in policy years two and above, since the premium used is the amount the policyholder would pay if no previous year's discounts apply. The calculation module thus consults the previous year's calculation to confirm that no such discount has been in place for the period immediately prior to the discount calculation. If it has, then instead of using actual premiums paid, send message to premium modules to calculate notional premium for this policyholder (including plan changes, family changes) as if no discount existed. As a check, the percentage discount for the year under consideration is applied to actual premiums paid and compared to the first value. If they do not match, the calculation is terminated pending manual checks. An automatic message will be sent to the party responsible for resolving this inconsistency.

Is the premium higher or lower than the previous calculation? If lower, then send additional message to ensure that an appropriate event occurred resulting in this change. This could be a change in cover or change to family make-up.

If premium volatility occurs around the time of calculation, there may be some doubt as to the exact quantum of premium to use in the formula. In this case, certain assumptions are necessary to allow the calculation to proceed. The use of averages and other "smoothing" strategies facilitates an approximation of the correct premium sum, and consequently the correct bonus amount.

The calculation program must take into account any volatility that may have existed in the makeup of the family unit covered by the health policy. Marriages, divorces, adding of dependents, and children becoming ineligible for coverage must all be carefully analysed by the calculation module. This then allows the calculation module to apply variants of the calculation formula to the cumulative premiums attracted by the policy during the period under scrutiny.

The calculation module is capable of interrogating the premium subsystem for this data and to then make sense of it for the purposes of bonus determination.

Get Claims

Figure 4B:
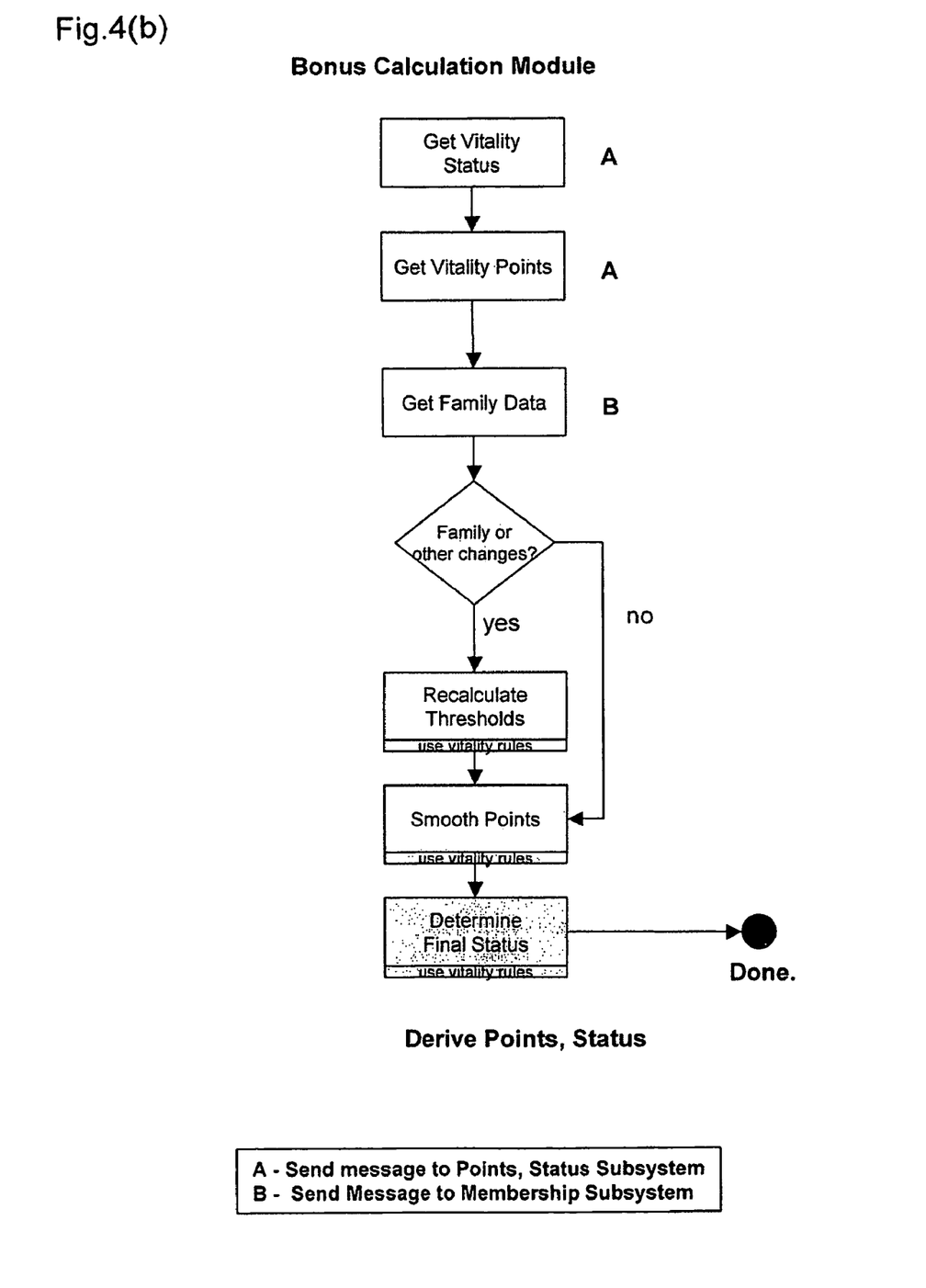

The bonus calculation module sends requests to the claims module subsystems as follows:

1. Preauthorisation subsystem: this will respond with data allowing the bonus calculation module to determine what levels of outstanding claims exposure remains in the system. The calculation module then splits all clinical events for the policyholder for the year into three categories:
   a. Those that are concluded (all claims paid)
   b. Those in progress (claims may have been partially paid)
   c. Those notified and authorised, but not yet claimed on.

The bonus calculation module will then impose rules to determine which claims to use in its calculations. Costs attached to different clinical scenarios differ depending on associated clinical predictability. For example, tonsillectomies always cost the same within acceptable margins of error. As another example, certain hospitalisations such as hip replacement may be complete, but the calculation module contains clinical knowledge indicating that a certain amount of follow-up physiotherapy is expected. In such clinical scenarios, and under certain criteria associated with the authorisation itself, the claims for incomplete events may be included in the bonus calculation.

2. Claims subsystem: Along with premiums, the exact quanta of claims paid to a policyholder is a primary operand within the bonus calculation. The calculation module will request all claims paid within a certain time period. All claims will then be checked against the clinical events as returned by the preauthorisation subsystem. Claims that cannot be associated with an event may indicate an error. The module contains rules to escalate potential errors to various parties capable of resolving them.

The calculation module also compares the overall number of claims for a particular policyholder to the total for a previous time period, typically the previous year. Significant changes to this value over time are indicative of additional errors. In certain cases, where policyholders are known to suffer from health issues which may be predicted to incur treatments (and thus claims) a drop in total claims for the calculation period would be flagged by the calculation module as a potential area for investigation.

An increase in claims volumes may be due to other factors other than ill-health. For example, a policyholder may have increased the number of policyholders on that policy. For large claims volumes, the calculation module will send messages to additional subsystems in an attempt to reconcile claims quanta with individual personal and/or clinical circumstances.

If a comparison between preauthorisations and claims results in some discrepancy, then the bonus calculation program will attempt to "smooth" claims to coincide with the clinical data recorded in the system. For example, if there is an expectation for a certain quanta of claims to be incurred by virtue of a preauthorised clinical event for which claims have not been received, the calculation module will make assumptions allowing it to treat undeceived claims as if they had been received more smoothly, i.e. in line with expectations.

Get Points, Status

Figure 4C:
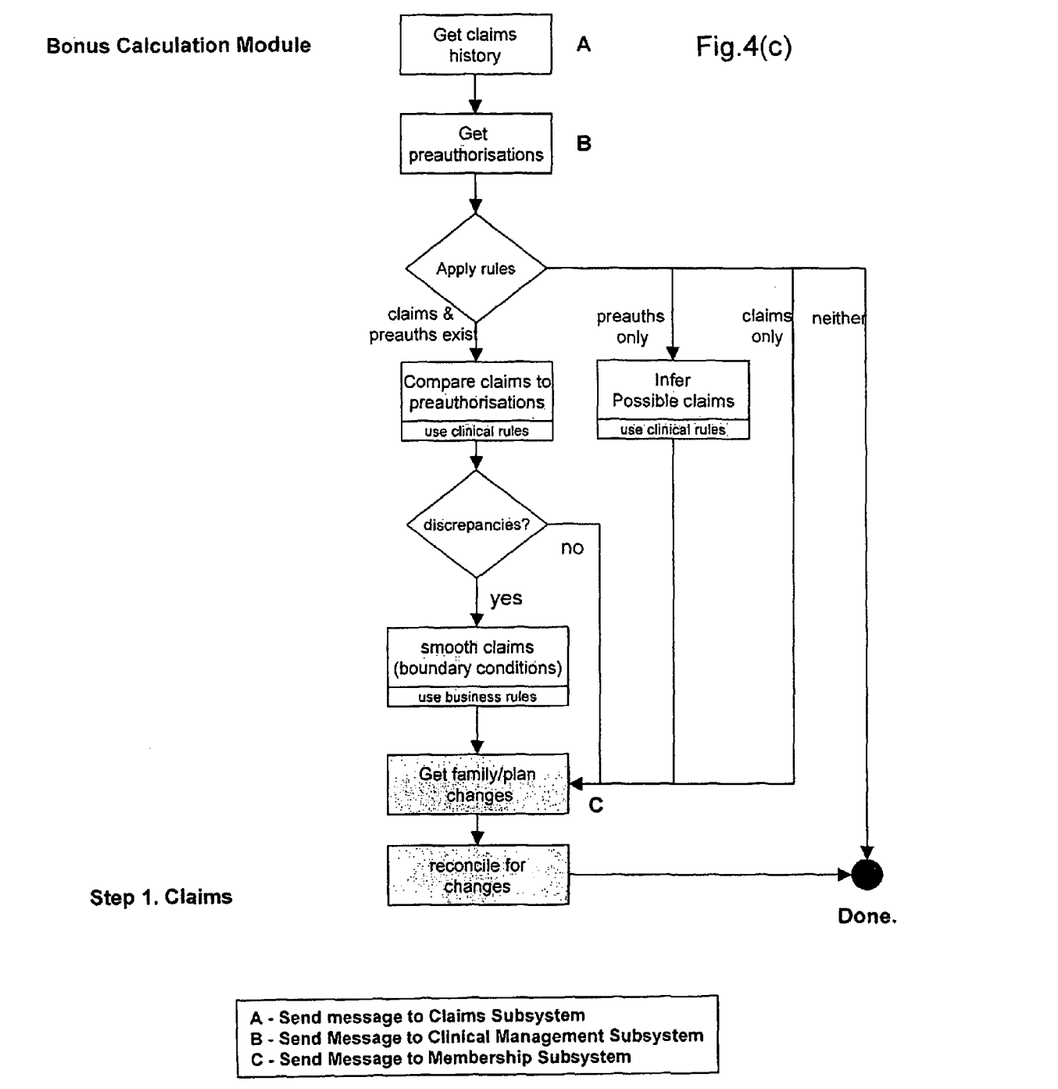

All points-accumulating activities will have been recorded by software during the bonus calculation period. The calculation module requires the total number of points which it uses to recalculate the "status" level based on a number of criteria.

For simple cases, the status is a function of point bands, which confer a certain "colou" status on the policyholder In cases where the policyholder may have been married or divorced (or divorced, then re-married), a more sophisticated calculation is required. Since status thresholds differ for singles and families, a pro-rating function recomputes the required threshold levels for a particular policy. This will be the final status levels used against points earned for the period under calculation Even more complicated cases may exist, which the calculation software can solve through the application of certain rules. For example, a married man may get divorced, and his (ex) wife may marry another policyholder (electing to transfer to that policy). In such cases, the points earned by the wife prior to divorce need to be allocated across both policies during the computation period. This allocation is performed thorough various formulae depending on the nature of the original points-scoring activities. Additionally, for activities for which maximum allowable points are imposed, applicable limits will need to be derived in order to compute a final points allocation for the policy.

Compute Bonus Amount

The bonus calculation module 16 will not proceed with the final calculation module until such time as the above parameters have been identified and resolved. The bonus calculation module contains the ability to identify how far it has progressed with the overall calculation, and can make visible the full set of partial activities performed. In addition, the calculation module will identify itself as being in a one of the following statuses:

Complete—simple calculation, no additional issues

Incomplete, but some issues pending, likely to be resolved automatically

Incomplete, but with non-serious issues requiring human intervention

Incomplete, critical issues remaining

The bonus available to the policyholder, once computed, is subject to a number of variations depending on the nature of the policy (individual, group) and the choices exercised by the individual (discounts, cash-back). This is described elsewhere.

The premium for the following year can then be computed. This is then a function of regular elements such as age, gender, geography and the cover that a policyholder has purchased. Added to this will be the elements of premium paid for the previous year, claims history and lifestyle history, as described herein. Derive Policy Message The computation of applicable low-claims discount results in a value available to be paid on a policy in accordance with the process and rules described above. This amount must then be communicated to the policyholder. The computation module is however also equipped to discern trends and to formulate an appropriate response to the policyholder.

For example, if a premium goes up markedly from one year to the next (i.e. policyholder loses discount), then this could be attributable to one of several factors:

Vitality status has dropped sharply, claims normal: in such circumstances, the calculation module will derive which points-earning activities have been curtailed or stopped, and will formulate an appropriate response to the policyholder. This would include reminders to attend a gym more frequently as may have been the case in the previous year. However, this needs to be compared with claims data to ensure that no inappropriate messages are generated: e.g. person had serious hip operation or worse Vitality status normal, high claims history: this would be a fairly normal scenario for low claimers that then experience a serious clinical situation or other elective surgery. The correct response in this case would be to indicate awareness of claims, with reminders of how the overall bonus scheme operates, such that the policyholder can set and achieve a more favourable ratio for the following year Hybrid models—moderate changes to points achieved as well as claims: in this case, emphasis would be placed on more general topics, rather than on points earning and claims issues alone.

Thus, the data processing system allows the managers of the medical insurance plan to calculate a premium for the coming year which is essentially linked to the amount of claims the policyholder has made from the insurance plan as well as to the health and fitness related activities leading to the earning of points.

We claim:

1. A computer implemented method for periodically determining a policyholder's discounted premium for a next succeeding period of a medical insurance plan comprising the steps of:

inputting into at least one computer data pertaining to (i) a medical insurance plan whereby policyholders in the plan pay periodically premiums for each succeeding period of the plan in consideration of their medical insurance claims for insured loss under the insurance plan will be paid according to the terms and conditions of the plan and the rules imposed by the plan, and (ii) a list of participating $3^{rd}$ parties and the goods and services provided which policyholders may avail themselves and receive points there for;

selecting, from data inputted into said at least one computer, at least one data pertaining to at least one policyholder, said data selected from the group consisting of: personal and family data, premiums paid in a current period and preceding periods, medical insurance claims made, goods and services of $3^{rd}$ parties which the policyholder has availed him/her self of, preselected medical testing of the policyholder, preselected health programs followed by the policyholder and results thereof, and points accumulated by the policyholder, the points based upon participation by the policyholder in beneficial health related activities;

calculating, using said at least one computer, premiums that a policyholder shall pay for each next succeeding period of each policyholder's medical insurance plan, based on the premium of the current period, by first determining a notional premium for the current period with no discount applied, and then, adjusting for any plan or option changes in personal and family data, and storing in memory of said at least one computer a first output indicative thereof;

calculating, using said at least one computer, for each policyholder (i) medical insurance claims paid during the current period, (ii) medical insurance claims filed and in process of resolution, and (iii) medical insurance claims filed but not yet in process of resolution, and applying plan rules inputted into said at least one computer to medical insurance claims in process of resolution and medical insurance claims not yet in process of resolution, and adjusting the policyholder's medical insurance claims for medical insurance claims deemed likely to comply with plan rules and be paid, to obtain an adjusted total of medical insurance claims, and storing in memory of said at least one computer a second output indicative thereof;

calculating, using said at least one computer, the status level of each policyholder based on the points accumulated by the policyholder, and storing in memory of said at least one computer a third output indicative thereof;

calculating, using said at least one computer, based upon the first, second and third outputs to the processor, a discounted premium to be applied to each policyholder's premium for the next succeeding period, and storing in memory of said at least one computer a fourth output indicative thereof; and transforming from memory in said at least one computer to human visible form, said fourth output, by one of displaying on a display or printing.

2. Apparatus for periodically determining a policyholder's discounted premium for a next succeeding period of a medical insurance plan comprising:

a. a data processing system comprised of a processor, a memory, an input device and a display;

b. means for implementing and storing in memory of the system (i) a medical insurance plan whereby policyholders in the plan pay periodically premiums for each succeeding period of the plan in consideration that medical insurance claims for insured loss for ill-health of the insured will be paid according to the terms and conditions of the plan and the rules imposed by the plan, and (ii) a list of participating $3^{rd}$ parties and the goods and services provided which policyholders may avail themselves and receive points there for;

c. means for recording in memory for each policyholder personal and family data, premiums paid in a current period and preceding periods, medical insurance claims made, goods and services of said participating $3^{rd}$ parties which the policyholder has availed him/her self, preselected medical testing, preselected health programs followed by the policyholder and results thereof, and all points accumulated by the policyholder;

d. means for recording in memory of the system (i) rate tables for medical insurance, (ii) risk factors, (iii) administration fees, (iv) expense allowances, (v) a points award schedule for participating $3^{rd}$ parties goods and services utilized by the policyholder, and a series of low to high graduated status levels based on points accumulated by a policyholder;

e. means for establishing a premiums module in said system for determining the premium that a policyholder shall pay for each next succeeding period of each policyholder's medical insurance plan, based on the premium of the current period, by first determining a notional premium for the current period with no discount applied, and then, adjusting for any plan or option changes in personal and family data, and providing and storing in memory a first output indicative thereof;

f. means for establishing a medical insurance claims module in the system for determining for each policyholder (i) medical insurance claims paid during the current period, (ii) medical insurance claims filed and in process of resolution, and (iii) medical insurance claims filed but not yet in process of resolution, and applying plan rules to medical insurance claims in process of resolution and medical insurance claims not yet in process of resolution, adjusting the policyholder's medical insurance claims for medical insurance claims deemed likely to comply with plan rules and be paid to obtain an adjusted total of medical insurance claims, and providing and storing in memory a second output indicative thereof;

g. means for establishing a bonus module in said system for determining the status level of each policyholder based on points accumulated by the policyholder, and providing and storing in memory a third output indicative thereof;

h. means for transmitting the first, second and third outputs to the processor and, based thereon, calculating a discounted premium to be charge each policyholder for the next succeeding period, and providing and storing in memory a fourth output indicative thereof; and i. means for displaying visually said fourth output by one of displaying on a display or printing.

3. Computer readable medium storing executable instructions that when executed causes the computer to periodically determine a policyholder's discounted premium for a next succeeding period of a medical insurance plan which has stored in memory of the computer a medical insurance plan, whereby policyholders in the plan pay periodically premiums for each succeeding period of the plan in consideration for which their medical insurance claims will be paid according to the terms and conditions of the plan, and the rules imposed by the plan:

a list of participating $3^{rd}$ parties and the goods and services provided which policyholders may avail themselves and receive points there for;

for each policyholder personal and family data, premiums paid in a current period and preceding periods, medical insurance claims made for coverage for ill-health, goods and services of said participating $3^{rd}$ parties which the policyholder has availed him/her self, preselected medical testing, preselected health programs followed by the policyholder and results thereof, and all points accumulated by the policyholder;

rate tables for medical insurance, risk factors, administration fees, expense allowances, a points award schedule for participating $3^{rd}$ parties goods and services utilized by a policyholder, and a series of low to high graduated status levels based on points accumulated by a policyholder;

a. first executable instructions that when executed determines via a premiums module the premium that a policyholder shall pay for each next succeeding period of each policyholder's medical insurance plan, based on the premium of the current period, by first determining a notional premium for the current period with no discount applied, and then, adjusts for any plan or option changes in personal and family data, and provides and stores in memory a first output indicative thereof;

b. second executable instructions that when executed determines via a medical insurance claims module for each policyholder (i) medical insurance claims paid during the current period, (ii) medical insurance claims filed and in process of resolution, and (iii) medical insurance claims filed but not yet in process of resolution, and applies plan rules to medical insurance claims in process of resolution and medical insurance claims not yet in process of resolution and in response thereto adjusts the policyholder's medical insurance claims for medical insurance claims deemed likely to comply with plan rules and be paid to obtain an adjusted total of medical insurance claims, and provides and stores in memory a second output indicative thereof;

c. third executable instructions that when executed determines via a bonus module the status level of each policyholder based on points accumulated by the policyholder, and provides and stores in memory a third output indicative thereof;

d. fourth executable instructions that when executed transmit the first, second and third outputs to the processor and, based thereon, calculates a discounted premium to charge each policyholder for the next succeeding period, and provides and stores in memory a fourth output indicative thereof; and e. fifth executable instructions that when executed displays visually said fourth output by one of displaying on a display or printing.

4. A computer implemented method for determining an insurance premium for a medical insurance policy, comprising:

selecting, from data inputted into at least one computer, at least one data pertaining to at least one insured including personal information, medical insurance claims paid for treatment of health issues, medical insurance claims filed and in process of resolution, medical insurance claims not yet in process of resolution, participation in beneficial health related activities, and plan rules;

calculating, using the at least one computer and the data inputted, medical insurance claims in process of resolution and medical insurance claims not yet in process of resolution, which are likely to comply with plan rules and be payable, to obtain data pertaining to a likely medical insurance claim total;

calculating, using the at least one computer and the data inputted, data pertaining to a participation status level of each of the at least one insured, based on the participation in health related activities;

calculating, using the at least one computer and the data inputted and calculated, including data pertaining to the likely medical insurance claim total and status level, a discounted premium to be applied to the at least one insured's premium due; and transforming from memory in the at least one computer to human visible form, the insured's premium due, by at least one of displaying on a display or printing;

wherein the at least one insured is incentivized to participate in health related activities, and a premium discount for the at least one insured based upon the participation reflects medical insurance claims for the insured that are likely to be paid.

5. The method of claim 4, wherein the step of calculating a likely medical insurance claim total, the likely medical insurance claim total is compared with medical insurance claims submitted by the at least one insured in a previous time period, as an error check.

6. The method of claim 4, wherein set step of calculating a likely medical insurance claim total includes the step of polling medical insurance claim data at predefined intervals.

7. The method of claim 4, wherein the step of calculating a participation status level includes assigning points to health related activities, and calculating a participation status level based on a total of points assigned based on the at least one insured's actual participation in health related activities assigned points.

8. The method of claim 7, wherein four participation status levels are assignable.

9. The method of claim 7, wherein a group of insureds is defined, wherein points assigned to insureds in the group are different than points assigned to insureds not in the group.

10. The method of claim 4, wherein the steps of calculating are performed close in time to a renewal date of the insurance policy.

11. The method of claim 4, further including the step of calculating a change in premium resulting from a change in a plan coverage for the insured, and using the calculated resulting change in premium in the step of calculating premium due.

12. The method of claim 4, further including the step of calculating likely errors in medical insurance claims paid, medical insurance claims in process, and medical insurance claims not in process, and correcting errors using inputted plan rules, or alerting individuals using the at least one computer to resolve the errors.

13. The method of claim 4, further including the step of calculating, using the at least one computer, a likely medical insurance claim status of complete, incomplete and likely to be resolved, incomplete requiring human intervention, and incomplete.

14. The method of claim 4, wherein said step of calculating premium due calculates a lower premium due using a lower likely medical insurance claim total than a premium due using a higher likely medical insurance claim total.

15. The method of claim 4, wherein said step of calculating premium due calculates a lower premium due using a higher participation status level than a premium due using a lower participation status level.

16. The method of claim 4, wherein said step of calculating premium due is carried out at an interval selected from the group consisting of: monthly, quarterly, biannually, and annually.

17. The method of claim 4, wherein said step of calculating premium due includes the step of splitting premium into an employer portion and an insured portion.

18. The method of claim 4, wherein a reduction in premium due is provided as cash back to the insured.

19. The method of claim 4, wherein said step of calculating premium due includes the step of smoothing premium data, to reduce the effect of volatility or discrepancy.

20. The method of claim 4, wherein said step of calculating a likely claim total includes the step of smoothing medical claim data, to reduce the effect of volatility or discrepancy.

* * * * *